United States Patent [19]

Kessler et al.

[11] Patent Number: 5,648,075
[45] Date of Patent: Jul. 15, 1997

[54] IODINE BASED GERMICIDAL COMPOSITION

[75] Inventors: Jack H. Kessler, Southborough; James C. Richards, Framingham, both of Mass.

[73] Assignee: Symbollon Corporation, Sudbury, Mass.

[21] Appl. No.: 684,334

[22] Filed: Jul. 19, 1996

Related U.S. Application Data

[63] Continuation of Ser. No. 324,391, Oct. 17, 1994, abandoned.

[51] Int. Cl.$^6$ .......................... A61K 38/44; A61K 33/36; C12N 9/96
[52] U.S. Cl. .......................... 424/94.4; 424/667; 435/188; 514/5
[58] Field of Search .................. 424/94.4, 667; 435/188; 514/5

[56] References Cited

U.S. PATENT DOCUMENTS

| | | | |
|---|---|---|---|
| 3,028,300 | 4/1962 | Cantor et al. | 167/17 |
| 4,227,161 | 10/1980 | Kessler | 424/94.4 |
| 4,271,149 | 6/1981 | Wincov et al. | 424/150 |
| 4,370,199 | 1/1983 | Orndoff | 162/161 |
| 4,576,817 | 3/1986 | Montgomery | 424/94 |
| 4,937,072 | 6/1990 | Kessler et al. | 424/94.4 |
| 4,996,146 | 2/1991 | Kessler | 435/28 |
| 5,169,455 | 12/1992 | Kessler | 134/42 |
| 5,185,371 | 2/1993 | Rubinstein | 422/28 |

OTHER PUBLICATIONS

Transfusion 1994 34: 322–327 entitled: Inactivation of lipid etc.

F.A. Highsmith Journal of Infectious Diseases vol. 167 p. 1027 1993.

Nunez & Pommier European Journal of Biochemistry vol. 7 pp. 286–293.

Morrison & Schonbaum Annual Review of Biochemistry vol. 45 pp. 851–888.

Ohtaki et al. Journal of Biochemistry vol. 256 pp. 805–810 1981.

*Primary Examiner*—John W. Rollins
*Assistant Examiner*—Deborah Ware

[57] ABSTRACT

The present invention relates generally to an enzymatically generated iodine microbiocide and more specifically to the use of such a microbiocide for the inactivation of pathogenic organisms that are contaminants in sensitive biological materials. The biocidal agent from the enzymatic reaction is free molecular iodine generated so as to (1) establish a minimum level above 10 ppm of free molecular iodine and (2) to establish defined ratios of free molecular iodine to other iodine species such that free molecular iodine comprises at least 10% of the total iodine species present on a molar basis.

5 Claims, No Drawings

IODINE BASED GERMICIDAL COMPOSITION

This application is a continuation of application Ser. No. 08/324,391, filed Oct. 17, 1994, now abandoned.

FIELD OF THE INVENTION

The present invention relates generally to the enzymatic formation of microbicide compositions that contain (1) a minimum level of free molecular iodine of above 10 ppm and a maximum level below 330 ppm and (2) defined ratios of free molecular iodine to other iodine species in order to inactivate pathogenic organisms. More specifically this application contemplates the use of an enzymatically generated iodine microbicide to inactivate pathogens that are contaminants in sensitive biological materials. A wide range of sensitive biological materials are contemplated under this application. These materials include cell lines used for tissue culture, whole blood, red blood cells, blood plasma, blood proteins, human cells such as sperm, human tissues such as skin and human organs. In order to be useful, a liquid microbicide should inactivate all unwanted pathogens and not substantially reduce the biological activity of the sensitive biological material of interest. The biocidal agent from the enzymatic reaction is free molecular iodine generated by the reaction of peroxidase, iodide and hydrogen peroxide.

DESCRIPTION OF THE RELATED ART

Sensitive biological products from human and animal sources are widely used for therapeutic, diagnostic and experimental purposes. Such products are subject to contamination by virtue of their natural environment which presents favorable conditions for microbial contamination and subsequent handling. Frequent contaminants include bacteria, viruses and fungi. Diagnostic tests for the presence of such pathogens are available but there has been no way to assure that these products are free from unwanted contaminants. A good example of this is the transfusion of human blood products which currently carries a well-known risk of transmitting a number of viruses and bacteria.

A large variety of chemical germicides have been used in the medical profession and biomedical industry to inactivate unwanted bacteria, viruses and fungi. The majority of these chemical germicides are either toxic or destructive to organic material and, as a result, these disinfectants are not suitable for use with sensitive biological materials. U.S. Pat. No. 5,185,371 describes a method to disinfect blood products that relies upon diluting a germicide in one of the following compositions: 0.9% aqueous sodium chloride, 5% aqueous dextrose, sugar solutions or other diluents that ameliorate the chemical incompatibilities of the liquid germicides with blood and blood products.

F. A. Highsmith et al. (*Journal of Infectious Diseases*, volume 167, page 1027, 1993) describes methods that utilize a chemically modified polyvinylpyrrolidone-iodine complex. The compositions and methods described in Highsmith have been used to disinfect blood products. The intuitive appeal of using iodine for such applications is obvious since iodine is a nutritional additive.

All of the prior art related to decontamination of sensitive biological materials with iodine containing compositions utilizes povidone-iodine or other complex chemical combinations that contain iodine either in the presence of high molecular weight polymers or bound to larger molecules. However, the prior art does not directly address the critical parameters required to effectively utilize iodine for the disinfection of biological materials. The key to effective use of iodine with sensitive biological materials in accordance with the present invention is to be able to control the level of free molecular iodine such that free molecular iodine is the principal iodine species present and to control the ratio of free molecular iodine to the other species of iodine present. In addition, it is highly preferred to substantially maintain the level of free molecular iodine under the conditions of pH that are not destructive to the biological materials.

In order for free molecular iodine to be effective, the level of this biocidal agent must be substantially maintained for a period of time that is sufficient to inactivate all of the unwanted pathogens. However, the chemical activity of free molecular iodine must be controlled in order to substantially maintain the integrity of the biological material of interest. The conflicting attributes of biocidal activity and biological compatibility require the practitioner to eliminate or minimize (1) other iodine species present which will contribute toxicity and chemical incompatibilities and do not necessarily contribute biocidal efficacy and (2) other non-biocidal chemicals since they serve as a potential source of contamination and incompatibility.

The pH that is most compatible with the overwhelming majority of biological materials contemplated under this application is pH 6.8 to 7.0. While it is not necessary to decontaminate the biological materials of interest precisely at a pH of 7.0, it is highly preferred to maintain a pH as close to 7.0 as possible to minimize the potential reduction in biological activity of the molecules of interest. However, a neutral pH introduces an additional factor that complicates the use of free molecular iodine in disinfection. Free molecular iodine is not stable at a neutral pH and, as a result, the duration of treatment is a critical parameter.

One of the disinfectants identified in U.S. Pat. No. 5,185,371 is 10% povidone-iodine which is frequently represented as PVP-$I_2$. PVP-$I_2$ is a complex of iodine with povidone. PVP-$I_2$ contains less than 9.0% by weight, and not more than 12% by weight of thiosulfate titratable iodine. In addition, PVP-$I_2$ typically contains not more than 6.6% by weight of iodide ions. Iodate and other inorganic species are typically added to PVP-$I_2$. As a result, PVP-$I_2$ contains all of the most common iodine species that are found in an aqueous environment including free molecular iodine, iodate, iodide, triiodide and hypoiodous acid. PVP-$I_2$ is available commercially from many different manufacturers and the pH of these products will vary by manufacturer. However, PVP-$I_2$ is strongly buffered at acidic conditions that typically range between pH 3.5 and 4.5.

The distribution of iodine species in PVP-$I_2$ does not favor its use for sensitive biological materials. PVP-$I_2$ is not a preferred degerming agent for biological materials since less than 0.2% of the iodine contained in such compositions is in the form of free molecular iodine. In addition, the pH of these compositions are toxic to most of the cells and tissues contemplated under this application. PVP-$I_2$ was designed to be applied directly to intact skin and the FDA approved use pattern is limited to intact skin. The epidermis of mammalians consists of dead cells that are significantly less sensitive to harsh chemicals than living cells.

U.S. Pat. No. 5,185,371 describes the treatment of blood and blood products with PVP-$I_2$ at concentrations that range from 0.01% to 0.5% by weight for up to 5 minutes.

This application proscribes a concentration range for PVP-$I_2$ that corresponds to a 1/200 to a 1/10,000 dilution of PVP-$I_2$. When PVP-$I_2$ is diluted in normal saline at 1/200 the pH of the resulting solution is≈4.6 and the level of free molecular iodine is≈10 ppm. When PVP-I$_2$ is diluted in normal saline at 1/10,000 the pH of the resulting solution is≈5.4 and the level of free molecular iodine is≈0–0.5 ppm. The combination of free molecular iodine, pH and contact time described in U.S. Pat. No. 5,185,371 is not adequate to effectively inactivate most of the bacteria and viruses of interest in the presence of a competing bioburden. It is known that a significant amount of iodine and/or extended contact times are required to completely inactivate non-lipid-enveloped viruses (Highsmith F. A. et at., *Transfusion*, volume 34, page 322, 1994).

Accordingly, there presently is a need to provide an iodine based method to disinfect sensitive biological materials including cell culture, human blood products, animal blood products and human and animal tissue products. Iodine based compositions have been formulated to disinfect sensitive biological materials but these compositions have several drawbacks. Iodine is an effective biocide and unlike other biocides, iodine is required for proper human nutrition and thyroid function. The difficulty with previous iodine based compositions is that they have unfavorable characteristics of pH and ionic strength and that active biocidal iodine (i.e., free molecular iodine) is (a) combined with other chemical species that are not biocidal and (b) not the predominant iodine species.

SUMMARY OF THE DISCLOSURE

The foregoing object of the present invention is accomplished by generating an iodine based microbicide in which there is a minimum level of free molecular iodine above 10 ppm and which comprises from 10% to 98% of the iodine species present on a molar basis. Another way to state this is that the iodine compositions will contain a plurality of iodine species with the molar ratio of free molecular iodine to other iodine species ranging from 10/100 to 98/100 and in a concentration range between 10 and 330 ppm. The preferred molar ratio of free molecular iodine to other iodine species should be above at least 25% and up to 98%. Such an iodine composition can be formed in an aqueous environment that is maximally compatible with a given biological material and will not only disinfect biological products but will do so without damage to the material of interest such as blood cells and tissue cells. It is presently believed that the disinfectant compositions of the present invention will render sensitive biological materials, e.g., tissue culture cells, safe, i.e., inactivate harmful bacteria, viruses and virus-like agents that may be present.

It is well known to those skilled in the art of tissue culture that mycoplasma organisms can contaminate cell cultures and can produce significant changes in tissue culture cells such as altered morphology, extended cell cycle and reduced output of specialized cell products such as monoclonal antibodies. Mycoplasma cells are distinguished from most other bacteria because they do not possess a cell wall. They are often found attached to the outer surface of a tissue culture cell membrane and in heavily contaminated cell cultures hundreds of mycoplasma organisms can be found coating the entire cell plasma membrane surface.

"Curing" a cell line from mycoplasma contamination refers to an effort to eliminate mycoplasma from tissue culture. A broad range of methods to eliminate mycoplasma contamination have been published including in vivo passage of tumor cell lines in nude mice, co-cultivation of infected cells with macrophages with or without antibiotics, induction of chromosomal damage in mycoplasma using 5-bromouracil and visible light, supplementation of culture media with specific antisera against mycoplasma and antibiotic treatment. It should be pointed out that experts in the field often recommend discarding mycoplasma contaminated cells whenever possible because the current cures are ineffective, impractical, cytotoxic or negatively affect the properties of cell lines. Nevertheless, the technician has no options in many cases because mycoplasma infected cells are often unique and irreplaceable. A method to cure infected cells lines from mycoplasma infection that does not generate resistance would be of great utility to the scientific community.

Iodine based germicides are well known in the art. The method used to generate the iodine based germicide of this application is to use peroxidase in combination with iodide and hydrogen peroxide. It is known from Kessler (U.S. Pat. Nos. 4,227,161, 5,169,455, 4,996,146 and 4,937,072), Orndoff (U.S. Pat. No. 4,370,199) and Montgomery (U.S. Pat. No. 4,576,817) that a combination of peroxidase, peroxide and iodide anions will form a bactericide in an aqueous environment. The bactericidal efficacy of this combination results from the enzymatic reaction that occurs when peroxidase, hydrogen peroxide and iodide react in solution. Peroxidase is known to effect the transfer of electrons from iodide to hydrogen peroxide. Hydrogen peroxide is converted into water by this reaction. Several possible reaction products have been postulated for the iodide anion including: 1) iodine free radicals (Nunez and Pommier, *European Journal of Biochemistry*, volume 7, pages 286–293, 1969); 2) hypoiodite ion (Morrison and Schonbaum, *Annual Review of Biochemistry*, volume 45, pages 861–888, 1976); and 3) iodinium ion (Ohtaki, Nakagawa, Kimura and Yamakazi, *Journal of Biochemistry*, volume 256, pages 805–810, 1981).

It has been observed that under certain conditions these peroxidase reactions will generate significant levels of free molecular iodine. The phrase "free molecular iodine" is a term of art that refers to elemental iodine, the chemical species that is represented as I$_2$ and that is capable of being titrated with sodium thiosulfate. It has been observed that it is possible to generate defined levels of free molecular iodine across a wide pH range using compositions comprised of peroxidase, peroxide and iodide. The exact level of available iodine in these compositions is a function of the concentration levels of peroxide, iodide, peroxidase, buffering agents, pH and other additives.

It is understood that if a material like red blood cells are to be disinfected, the disinfectant composition must be substantially isotonic so as to eliminate the potential for damage to the red blood cells. The disinfectant concentration and the time required to effectively inactivate any pathogenic organisms is dependent upon the level of free molecular iodine in the final environment. Suitable concentrations of free molecular iodine are a function of the precise biological material of interest. In general the range of free molecular iodine that is suitable is between 10 and 330 ppm. The amount of contact time required to inactivate the pathogenic organisms of interest is a direct function of the level of free molecular iodine, the pathogens of interest and the level of biological material in the composition.

After contacting the sensitive biological material of interest with free molecular iodine, the free molecular iodine is allowed to dissipate via hydrolysis in the composition. Alternatively, the iodine in the composition can be separated by a plurality of means that are familiar to one skilled in the art including adding materials, like cyclodextrin, that bind iodine or passing the composition of columns that contain iodine binding materials.

DETAILED DESCRIPTION OF THE INVENTION

A method is provided in which most types of pathogenic organisms in presence of sensitive biological material are completely inactivated. Additionally, the biological materials may be used subsequently for therapeutic or diagnostic purposes. The invention is based, in part, upon the unexpected discovery that elevated concentrations of free molecular iodine are compatible with many sensitive biological materials including, but not limited to, red blood cells, leukocytes, platelets, human embryonic lung cells, HeLa, Hep-2 cells, BSC-1 cells, WI-38 cells, CHO cells and astrocytes.

In accordance with this invention free molecular iodine is generated and contacted with the biological material of interest. The level of free molecular iodine that is required to be in contact with the contaminated material is between 10 and 330 ppm. The compositions contemplated under this application will have a molar ratio of free molecular iodine to other iodine species that ranges from 10/100 to 98/100. In order to optimally convert iodide into free molecular iodine the ratio of hydrogen peroxide to iodide is preferably established with a molar ratio that is less than 4; the optimal molar ratio of hydrogen peroxide to iodide that can be initially established is a 1/2 ratio. The pH of the aqueous environment must be controlled to be between pH 5.5 and 7.5. The preferred pH range in which to treat the biological material of interest is between pH 6.0 and 7.0. The contact time for the free molecular iodine can be varied widely and will depend upon the level of organic material in the composition and the temperature at which the material is treated. The contact time and temperature of treatment must be derived empirically for each application.

Free molecular iodine is generated by using peroxidase, iodide, and a source of hydrogen peroxide. It is obvious that the concentration of free molecular iodine used must be adequate to inactivate the contaminating pathogens; however, what is less obvious and equally critical is to generate an iodine based germicide whose principal component is free molecular iodine. By contacting the material of interest with an iodine composition that is principally free molecular iodine one minimizes the potential for chemical incompatibilities and contamination. Free molecular iodine should comprise at least 10% on a molar basis of all of the iodine species present after the iodine based germicide has been placed in an aqueous environment with the biological material of interest.

The reactants that comprise the peroxidase catalyzed oxidation of iodide must be controlled to yield a suitable result. The reaction should be established so as to efficiently convert iodide ions into free molecular iodine. Additionally, it is preferable to establish reaction conditions that convert at least 50% of the initial concentration of hydrogen peroxide into water and in no event should the concentration of hydrogen peroxide that is in contact with the biological material of interest be above a level of 0.015%. In order to optimally convert iodide into free molecular iodine the molar ratio of hydrogen peroxide to iodide should be initially established in a 1/2 proportion. It is highly preferred to limit this ratio to no greater than 4.

The preferred oxidant of this invention is hydrogen peroxide. Any material which acts as a source of hydrogen peroxide when admixed in an aqueous environment is suitable for the present invention. The term "source of peroxide" for purposes of the present invention and as used herein shall mean any material alone or in combination which can serve as precursors for hydrogen peroxide including metal peroxides, percarbonates, persulphates, perphosphates, peroxyesters, urea peroxide, peroxyacids, alkylperoxides, acylperoxides and perborates. Alternatively methyl peroxide can also be used as a source of hydrogen peroxide. Mixtures of two or more of these substances can also be used. The concentration range .for hydrogen peroxide in the final composition is between 0.005 and 0.025% in the final composition prior to initiation of the oxidation of iodide. The preferred concentration for hydrogen peroxide is between 0.001 and 0.01% in the final composition prior to initiation of the oxidation of iodide.

The donor molecule of this invention is iodide anion. Suitable dry sources of iodide anion for this invention include sodium iodide and potassium iodide as well as other salts of iodide. Any compound which yields iodide anion upon dissolution in an aqueous environment is suitable for this application. The simple salts of iodide are preferred and have the advantage of being less costly. Additionally, they have a long shelf life in solid form.

Iodide anion can be provided to the system in a liquid form if it is kept stable prior to use. Specifically, it is preferred not to contact the iodide anion with hydrogen peroxide. The concentration iodide that will yield a suitable level of iodine varies with the pH of the contemplated formulation. In addition, the required iodide level will vary dramatically depending upon the ratio of peroxide to iodide. When the preferred ratio of hydrogen peroxide to iodide of 1/2 is used, the preferred range for iodide anions is between 0.01 and 0.35 grams per liter in the final reconstituted formulation prior to initiation of the enzymatic reaction. However, for some contemplated applications it is possible to less effectively convert iodide into free molecular iodine and therefore the potentially useful range is for iodide is between 0.01 and 0.7 grams per liter in the final reconstituted formulation prior to initiation of the enzymatic reaction. These ranges of iodide anion in conjunction with pH and the concentration of the other additives are anticipated to yield a concentration of free molecular iodine within a range of 10 to 330 ppm.

The peroxidase enzyme of this invention is identified by the International Union of Biochemistry and the International Union of Pure and Applied Chemistry by the Enzyme Commission identification No. E.C. 1.11.1.7. Peroxidase can be obtained from a wide variety of sources. These sources include milk (lactoperoxidase) and human leukocytes (myerloperoxidase). The least expensive and most robust peroxidase suitable for this application is horseradish peroxidase. Commercially obtained peroxidase comes lyophilized as a dry powder which can then be admixed in a suitable carrier. It is anticipated that peroxidase that has been cloned from either horseradish, milk or human leukocytes will be suitable as a source of peroxidase for this application. Additionally, it has been observed that chemically modified peroxidase is suitable for use in this application. Modifications to the amino, carboxyl or carbohydrate moieties yield a suitable catalytic agent for inclusion in this application. The chemical modifications to peroxidase include cross-linking of enzyme molecules to each other, to solid surfaces or to other proteins. The chemical agents used for crosslinking include glutaraldehyde, maleimides, succinimides, carbodiimides, dicarboxylates, activated glycols, imidoesters, photoreactive azides and other agents known to one skilled in the art.

The aforementioned forms of peroxidase can be provided in a dry form such as the lyophilized peroxidase offered commercially or in a largely aqueous environment. If the peroxidase is supplied in an aqueous environment it typically will be incorporated into a medium that provides increased stability such as glycerol, dextrans, or other polyols or sugars with elevated viscosity. The peroxidase of this application can be combined with many additives whether it is supplied dry or in an aqueous environment. The concentration range that peroxidase can be used over is between 0.00005 and 0.005 mg/mL in the final composition. The preferred range is between 0.0005 and 0.01 mg/mL in the final composition.

Suitable buffering agents for inclusion in the compositions contemplated in this application include water and hydroalcoholic mixtures buffered with glycine-glycine. HCl, potassium hydrogen phthalate-phthalic acid, citric acid-$Na_2HPO_4$, citric acid-$KH_2PO_4$-$H_3BO_3$-diethylbarbituric acid-NaOH, citric acid-sodium titrate, dimethylglutaric acid-sodium dimethylglutarate, acetic acid-sodium acetate, succinic acid-sodium succinate, potassium hydrogen phthalate-dipotassium phthalate, sodium cacodylate-cacodylic acid, sodium hydrogen maleate-disodium maleate, $Na_2HPO_4$-$NaH_2PO_4$, sodium bicarbonate-5% $CO_2$, imidazole-imidazole.HCl, boric acid-sodium borate, and the following buffers known to one skilled in the art as Good buffers Tris, MES, BIS-TRIS, AD& ACES and PIPES.

If the biological material of interest is a mammalian cell then after the free molecular iodine composition and cells are mixed sufficiently to inactivate any pathogens that may be present, the iodine composition can be separated from the cells. The separation preferentially involves washing the cells in an automated cell washer or semi-automated cell washer with an isotonic solution until the disinfectant is substantially removed. Alternatively, one can concentrate cells using a simple benchtop centrifuge, decant the supernatant that substantially contains the iodine germicide, and resuspend the cells in a medium of choice.

In a case where the sensitive biological materials consist of proteins, the iodine based germicide may be separated by precipitating our the plasma proteins in a generally conventional fashion or by passing the entire composition through a chromatographic separation medium which are very well known to one skilled in the art or by dialysis.

All of the foregoing operational principles and advantages of the present invention will be more fully appreciated upon consideration of the following detailed examples.

Example 1

Iodine based compositions were prepared that consisted principally of free molecular iodine. These compositions were prepared by incubating horseradish peroxidase, sodium iodide and hydrogen peroxide at a pH of 5.5. Allowing these materials to incubate for a defined time period and then performing an analytical characterization of the resulting formulation.

The concentration of the following three iodine species was measured: free molecular iodine, triiodide and iodide anion. Free molecular iodine was measured potentiometrically by the published method of Gottardi (Gottardi W., Fresenius Z. Anal Chem., volume 314, page 582, 1983). Two Corning model 345 pH meters were used to make the potentiometric measurements. The Corning electrodes that were used included a standard platinum electrode, a reference electrode and an iodide ion selective electrode. Triiodide was determined by performing a sodium thiosulfate titration to determine the level of total iodine and then subtracting the level of free molecular iodine from the total iodine level. The iodide ion concentration was determined directly by using a Corning iodide ion selective electrode.

There were three conditions performed in a citrate buffer at a pH of 5.5. All conditions used a final concentration of 5 ug/mL of horseradish peroxidase. The first condition (Treatment No. 1) used a concentration of sodium iodide that was 60 mg per liter and an equal molarity of hydrogen peroxide that was established using sodium percarbonate (0.025 grams per liter) as the source of hydrogen peroxide. Conditions two and three (Treatment Nos. 2 & 3) used 200 and 450 mg per liter of sodium iodide and 0.0833 and 0.187 grams per liter of sodium percarbonate respectively. The solutions were allowed to incubate for 60 minutes and the analytical measurements were made. The results were as follows:

| ppm of Iodine Species | | |
|---|---|---|
| $I_2$-Iodine | $I_3^-$-Triiodide | $I^-$-Iodide |
| Treatment 1 | | |
| 46.6 | <2 | 0.126 |
| Treatment 2 | | |
| 128 | <2 | 0.476 |
| Treatment 3 | | |
| 290 | 324 | 0.650 |

Conclusion: It is possible to generate peroxidase based iodine germicides that are principally comprised of free molecular iodine and the ratio office molecular iodine to the other species can be controlled.

Example 2

Iodine based compositions were prepared at a pH of 7.0 that consisted principally of free molecular iodine. These compositions were prepared by incubating horseradish peroxidase, sodium iodide and hydrogen peroxide at a pH of 7.0. These components were allowed to incubate for a defined time period and then analytical determinations were performed on the resulting composition. The weights and volumes of the chemical components used were: 0.2 grams of anhydrous citric acid, weighed our, 1.3 mL of 3% hydrogen peroxide, 100 mg of sodium bicarbonate and 3 mg of horseradish peroxidase. The composition was allowed to incubate for 15 minutes prior to performing the analytical determinations described in experiment 1. The results are shown below:

| ppm of Iodine Species | | |
|---|---|---|
| $I_2$-Iodine | $I_3^-$-Triiodide | $I^-$-Iodide |
| 178 | 72 | 0.82 |

Conclusion: It is possible to generate iodine based germicides at a pH of 7.0 that are principally comprised of free molecular iodine.

Example 3

The three formulations described in experiment 1 were tested to determine their ability to inactivate Staphylococcus aureus in the presence of $10^6$ red blood cells (RBC) per mL. The effect that these formulations had on the cellular morphology of the RBCs was determined by microscopic examination. A control experiment was performed using 10% PVP-$I_2$ at four dilutions that ranged from 1/20 to 1/10,000.

Whole blood was processed by the Ficoll lymphocyte isolation procedure. The red blood cells (RBC) were recovered and washed once with phosphate buffered saline and held at a concentration of $3.5 \times 10^9$ RBC/mL in Alsevers solution at 5° C.

Agar plates were inoculated by washing the growth from Staphylococcus aureus slants with 5 mL of 0.25 molar phosphate buffer dilution water at a pH of 7.0 (PBDW) into 100 mL of PBDW. One mL of this suspension was added to each of 7 nutrient agar plates which were incubated for 18-24 hr at 35°-37°. Bacterial colonies were removed from the agar surface using 1 mL of PBDW and a sterile swab. The suspension was standardized to give about 109 cfu/mL using a Milton-Roy Spec 20 spectrophotometer.

One hundred mL of each test germicide were equilibrated to 25° C. in a water bath. Two minutes prior to the start of the assay, RBCs were added at a level of $10^6$ RBCs/mL. S. aureus was added to a level of $2.0 \times 10^8$ cfu/mL. One mL samples were removed after 30, 60, 120, and 300 second exposures and neutralized in 10 mLs 0.5% thiosulfate. One mL and 0.1 mL of the neutralized samples were pour plated in quadruplicate using Plate Count Agar.

Inactivation of Staphylococcus aureus in the Presence of Red Blood Cells

| Timepoint | Dilution of 10% PVP-I$_2$ | | | | Peroxidase Germicide Free Iodine Level | | |
|---|---|---|---|---|---|---|---|
| | 1:20 | 1:100 | 1:200 | 1:1,000 | 10 | 63 | 114 |
| 30 seconds | pass | pass | fail | fail | fail | pass | pass |
| 60 seconds | | | pass | fail | fail | | |
| 120 seconds | | | | fail | fail | | |
| 300 seconds | | | | fail | pass | | |

This experiment determined the ability of the disinfectant to inactivate at least $10^6$ cfu/m of Staphylococcus aureus. The results of these measurements are shown above. All of the disinfectants were effective against the Staphylococcus aureus with the exception of 10% PVP-I$_2$ at a 1/1,000 dilution. The peroxidase based iodine germicide exhibited a 6 log reduction of Staphylococcus aureus within 30 seconds at free molecular iodine levels of 63 and 114 ppm; at a free molecular iodine level of 13 ppm the peroxidase based iodine germicide required 5 minutes to effect a 6 log inactivation of Staphylococcus aureus.

Microscopic examination of the RBCs treated with the peroxidase based iodine germicide RBC showed no morphologic changes or reduction in counts of the cells. The RBCs treated with 10% PVP-I$_2$ appeared discolored and shriveled with no reduction in count except for the 10% PVP-I$_2$ sample that was diluted 1/1000. The level of free molecular iodine in the 1/1000 dilution of 10% PVP-I$_2$ was determined to be 6 ppm.

Example 4

An enzyme based iodine germicide was generated and its ability to inactivate viruses in the presence of a high concentration of red blood cells in human serum was determined. The germicide was made by dissolving 450 mg of sodium iodide in one liter of 0.05 molar citrate buffer at pH 5.5 and then simultaneously dissolving 10 mg of horseradish peroxidase (Sigma No. P8125) and 187 mg of sodium iodide. This solution was allowed to incubate for 10 minutes and then the virucidal efficacy of this formulation was determined.

Whole blood was processed by the Ficoll lymphocyte isolation procedure. The red blood cells (RBC) were recovered and washed once with phosphate buffered saline and held at a concentration of $6.5 \times 10^9$ RBC/mL in Alsevers solution at 5° C.

The tissue culture ineffective dose 50 (TCID$_{50}$) is the concentration of virus particles that causes 50% of a series of cultures to be infected. About $10^7$ units of TCID$_{50}$ vesicular stomatitis virus were added to samples of pooled human serum that contained $10^6$ RBCs per mL. This sample was incubated with the germicide for 5 minutes at 4° C. and at 25° C. After five minutes the virus titter was determined as follows. In quadruplicate, the sample was serially diluted fivefold in minimal essential media (MEM) nonessential amino acids solution containing 10% fetal calf serum and 0.1% sodium thiosulfate. The dilutions were plated onto 96-well plates containing Vero cells (ATCC CRL81) at approximately 80% confluency. The lowest dilution used in this assay was 1:5 of the original treated serum. The cultures were incubated for 3 days at 37° C. in a 5% CO$_2$ atmosphere and each well was examined for a cytopathic effect. At both 4° and 25° C. no cytopathic effect was observed in mock infected and iodine-treated tissue culture wells. This indicates that the germicide was effective in inactivating a lipid enveloped virus in the presence of sensitive biological material. The effect that these formulations had on the cellular morphology of the red blood cells was determined by microscopic examination. Microscopic examination of the red blood cells indicated that the peroxidase based iodine germicide did not cause a morphologic change or reduce the number of RBCs. None of the treated cells appeared discolored or shriveled. p Example 5

In the present example we demonstrate a simple, safe and effective method for killing mycoplasma in cell culture without any harmful changes in the mammalian cells. The peroxidase based iodine germicide described in this application was used in the present example to kill Mycoplasma hominis in the presence of human cells in vitro. A human cell line Hep-2 was experimentally infected with Mycoplasma hominis. Mycoplasma hominis is a typical representative of the Mycoplasma spp. genus. Mycoplasma infected and uninfected Hep-2 cells were grown in standard MEM supplemented with 5% fetal calf serum (FCS). Antibiotics were not used. Mycoplasma contamination was verified by fluorescent microscopy (stained with Hoechst dye number 33258) and by standard microbial cultivation in broth and agar.

One liter of distilled water was added to a glass beaker. Five milligrams of horseradish peroxidase was added to the beaker and dissolved. Forty two milligrams of sodium percarbonate was added to the solution and the pH was adjusted with citric acid to a final pH of 6.1. Sixty milligrams of sodium iodide was added to the solution and dissolved; this established a molar ratio of approximately 1/2 between hydrogen peroxide and iodide. This solution was allowed to incubate at room temperature for 5 minutes and then it was used as indicated below.

The peroxidase based iodine germicide at a pH of 6. was used to wash cell pellets at each passage. Cell monolayers were dispersed with saline-trypsin and concentrated by centrifugation. Cell pellets were resuspended into 10mL of the iodine germicide, mixed by vortex agitation and cells were pelleted by centrifugation. The total treatment time was 15 minutes including centrifugation.

Infected and uninfected cells were evaluated by fluorescent microscopy and microbial cultivation after each cell passage. Two surprising and unexpected results were observed. Treated Hep-2 cell morphology, growth characteristics and overall monolayer appearance were indistinguishable from untreated Hep-2 cells. One significant effect of the free molecular iodine treatment was that treated cells appeared "stained or tanned". However, the staining dissipates and treated cells are indistinguishable from untreated cells within 2 hours post treatment. *Mycoplasma hominis* was completely killed in all trials after either one or two treatments. When treated and untreated cells were stained and evaluated by fluorescent microscopy we occasionally observed stained mycoplasma associated with cells in iodine-treated cultures. However, mycoplasma could not be grown from treated cell cultures. A summary of the data is shown in the table below.

|  | Mycoplasma Infected Hep-2 Cells | Uninfected HEP-2 Cells |
|---|---|---|
|  | Trial 1 | |
| Peroxidase-iodine germicide in Hanks buffer | stain = + culture negative | stain = – culture negative |
|  | Trial 2 | |
|  | stain = + culture negative | stain = – culture negative |
|  | Trial 1 | |
| Control without germicide in Hanks buffer | stain = ++++ culture positive | stain = – culture negative |
|  | Trail 2 | |
|  | stain = ++++ culture positive | stain = – culture negative |

– = no stained mycoplasma cells
+ = 1 fluorescent spot per 20 cells
++ = 1 fluorescent spot per 1 cells
+++ = 10 fluorescent spots per cell
+++ = >100 spots per fluorescent cell

We claim:

1. An iodine based germicidal composition for disinfecting pathogenic organisms in or on sensitive biological materials when admixed with an aqueous based medium consisting essentially of a peroxidase selected from the Enzyme Commission No. E.C. 1.11.1.7, a source of hydrogen peroxide and an iodide source in a molar ratio of hydrogen peroxide to iodide of between about 0.5 to 4.0 and having a maximum concentration of hydrogen peroxide at the formation of said admixture of 0.015% such that a plurality of iodine species are formed having a molar ratio of at least 25% and up to 98% free molecular iodine and a free molecular iodine concentration of between 10 and 330 ppm.

2. The iodine based germicidal composition of claim 1 wherein the initial molar ratio of hydrogen peroxide to iodine is about 0.5.

3. The iodine based germicidal composition of claim 1 further comprising a buffering agent to maintain a pH for said composition of between pH 5.5 and 7.5.

4. The iodine based germicidal composition of claim 3 wherein said pH is maintained above 6 and below 7.5.

5. The iodine based germicidal composition of claim 4 wherein said buffering agent is selected from the group consisting of glycine, phthalate acid, citric acid, phosphate, borate, barbituric acid, glutaric acid, dimethylglutarate, acetic acid, sodium acetate, succinic acid-sodium succinate, cacodylic acid, sodium hydrogen maleate, sodium bicarbonate, imidazole, TRIS (tris(hydroxymethyl) aminoethane), MES (2-[N-morpholino]ethanesulfonic acid), BIS-TRIS (bis[2-hydroxyethyl]imino-tris[hydroxymethyl] methane; 2-bis[2-hydroxyethyl]amino-2-[hydroxymethyl]-1,3-propanediol), ADA (N-[2-acetamido]-2-iminodiacetic acid; N-[carbamoylmethyl]iminodiacetic acid), ACES ((2-[(2-amino-2-oxoethyl)-amino]ethanesulfonic acid; N-[2-acetamido]-2-aminoethane-sulfonic acid) and PIPES (piperazine-N, N-bis[2-ethanesulfonic acid]; 1,4-piperazinediethanesulfonic acid).

* * * * *